(12) United States Patent
Yamaya et al.

(10) Patent No.: US 9,538,964 B2
(45) Date of Patent: Jan. 10, 2017

(54) INCLINED PET DEVICE AND PET COMBINED DEVICE

(75) Inventors: Taiga Yamaya, Chiba (JP); Hideaki Tashima, Chiba (JP); Mitsuo Watanabe, Hamamatsu (JP); Eiichi Tanaka, Hamamatsu (JP)

(73) Assignees: NATIONAL INSTITUTES FOR QUANTUM AND RADIOLOGICAL SCIENCE AND TECHNOLOGY, Chiba-shi (JP); HAMAMATSU PHOTONICS K.K., Hamamatsu-shi (JP)

( * ) Notice: Subject to any disclaimer, the term of this patent is extended or adjusted under 35 U.S.C. 154(b) by 76 days.

(21) Appl. No.: 14/113,334

(22) PCT Filed: May 30, 2011

(86) PCT No.: PCT/JP2011/062394
§ 371 (c)(1),
(2), (4) Date: Oct. 22, 2013

(87) PCT Pub. No.: WO2012/164664
PCT Pub. Date: Dec. 6, 2012

(65) Prior Publication Data
US 2014/0046180 A1 Feb. 13, 2014

(51) Int. Cl.
*A61B 6/03* (2006.01)
*G01T 1/29* (2006.01)
(Continued)

(52) U.S. Cl.
CPC ............. *A61B 6/037* (2013.01); *A61B 6/4258* (2013.01); *A61B 6/4275* (2013.01);
(Continued)

(58) Field of Classification Search
CPC ........... A61B 6/025; A61B 6/037; A61B 6/40; A61B 6/42; A61B 6/4241; A61B 6/4417; A61B 6/4441; A61B 6/5229
(Continued)

(56) References Cited

U.S. PATENT DOCUMENTS

| 2009/0032714 A1 | 2/2009 | Peter et al. |
| 2009/0039268 A1 | 2/2009 | Peter et al. |

(Continued)

FOREIGN PATENT DOCUMENTS

| JP | U-02-122378 | 10/1990 |
| JP | A-2008-538312 | 10/2008 |

(Continued)

OTHER PUBLICATIONS

Crespo et al., "On the detector arrangement for in-beam PET for hadron therapy monitoring," *Physics in Medicine and Biology*, vol. 51, pp. 2143-2163, 2006.

(Continued)

*Primary Examiner* — Peter Luong
(74) *Attorney, Agent, or Firm* — Oliff PLC

(57) ABSTRACT

An inclined PET device is provided in which the cut plane of a detector ring upon which a plurality of PET detectors are disposed is inclined so that it does not intersect perpendicularly with the long axis of a bed that carries a subject to be examined and in which an open space that passes through the bed in a direction perpendicular to the long axis thereof is formed, in order to enable access to the subject to be examined. The PET detectors are disposed and stacked in a direction parallel to the long axis of the bed. Thereby, the number of PET detectors is reduced and device cost is reduced, while the detector ring as well as the device can be (Continued)

miniaturized. At the same time, the open space that passes through the bed in a direction perpendicular to the long axis can be preserved.

22 Claims, 27 Drawing Sheets

(51) Int. Cl.
*A61B 6/00* (2006.01)
*A61N 5/10* (2006.01)

(52) U.S. Cl.
CPC .......... *A61B 6/4447* (2013.01); *A61N 5/1077* (2013.01); *G01T 1/2985* (2013.01); *A61N 2005/1052* (2013.01)

(58) Field of Classification Search
USPC ................................................ 600/407, 436
See application file for complete search history.

(56) References Cited

U.S. PATENT DOCUMENTS

2009/0074151 A1* 3/2009 Henderson et al. .......... 378/198
2010/0128956 A1 5/2010 Yamaya et al.
2011/0240867 A1* 10/2011 Tonami ......................... 250/366
2012/0150018 A1* 6/2012 Yamaya ............... A61N 5/1049
600/411

FOREIGN PATENT DOCUMENTS

| | | |
|---|---|---|
| JP | A-2009-042029 | 2/2009 |
| JP | A-2010-094421 | 4/2010 |
| JP | A-2010-101666 | 5/2010 |
| JP | A-2010-223956 | 10/2010 |
| JP | A-2011-069636 | 4/2011 |
| WO | WO 2008/129666 A1 | 10/2008 |
| WO | WO 2009/122561 A1 | 10/2009 |
| WO | WO 2010/016107 A1 | 2/2010 |

OTHER PUBLICATIONS

International Search Report issued in Application No. PCT/JP2011/062394; Dated Jun. 28, 2011 (With Translation).
Dec. 2, 2013 International Preliminary Report on Patentability issued in International Application No. PCT/ JP2011/062394.

* cited by examiner

Fig.5
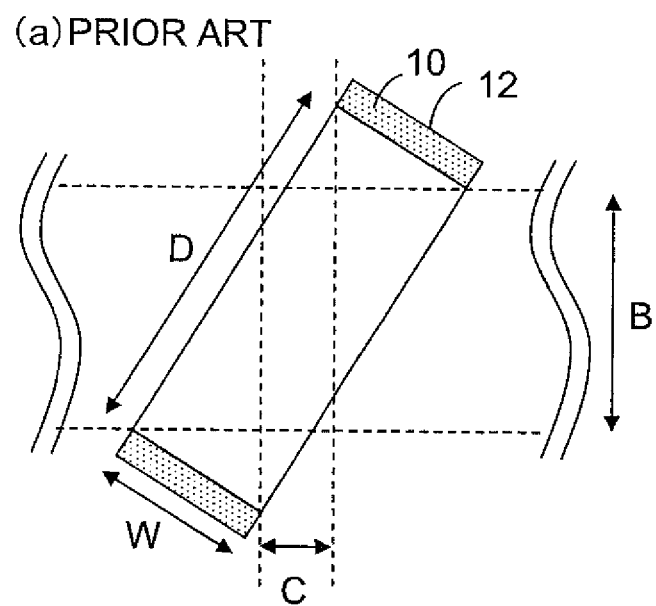
(a) PRIOR ART
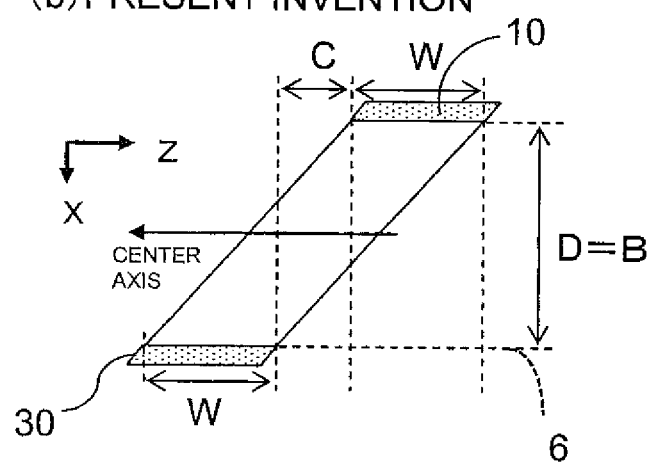
(b) PRESENT INVENTION

Fig.7
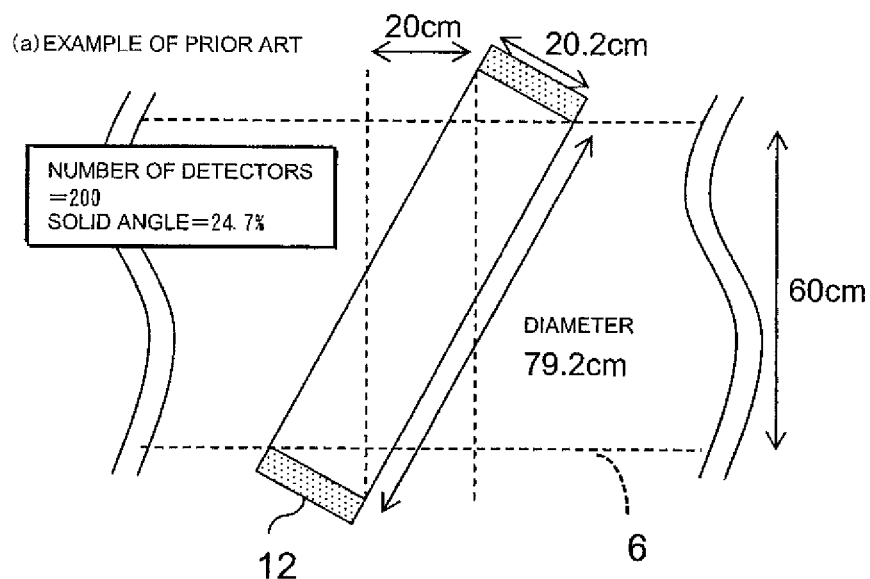
(a) EXAMPLE OF PRIOR ART
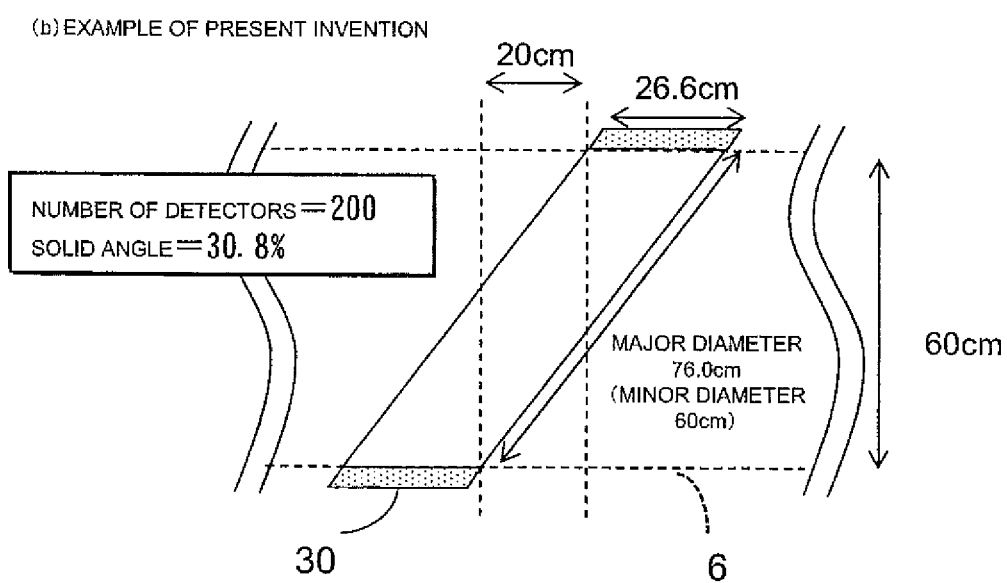
(b) EXAMPLE OF PRESENT INVENTION Fig.12
(a)
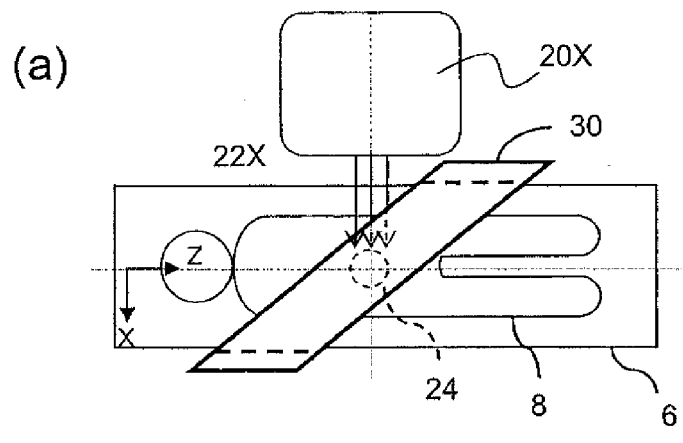
(b)
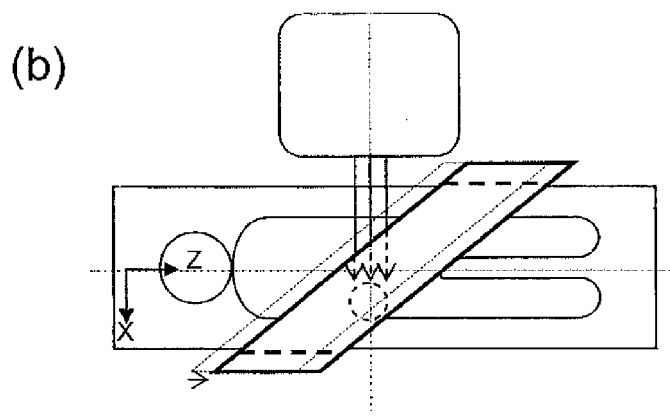
(c)
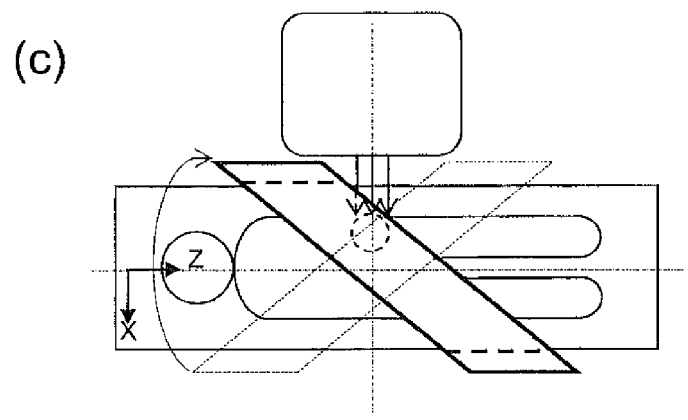

Fig.15
(a) HORIZONTAL IRRADIATION
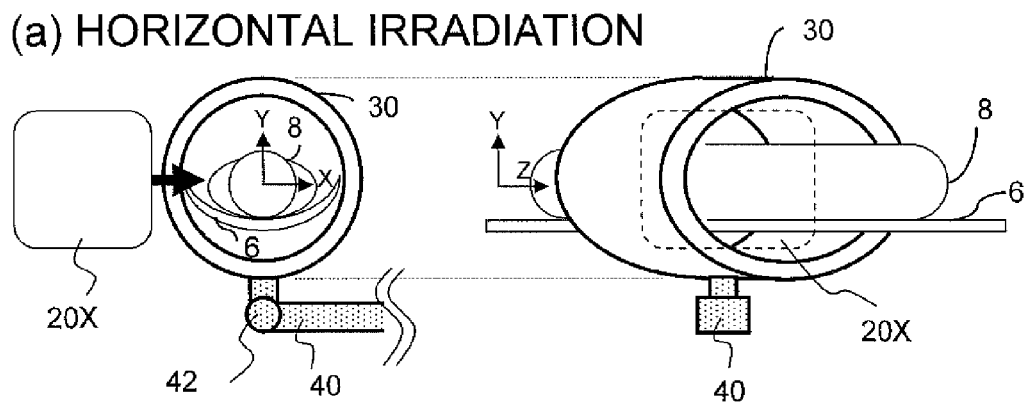
(b) VERTICAL IRRADIATION
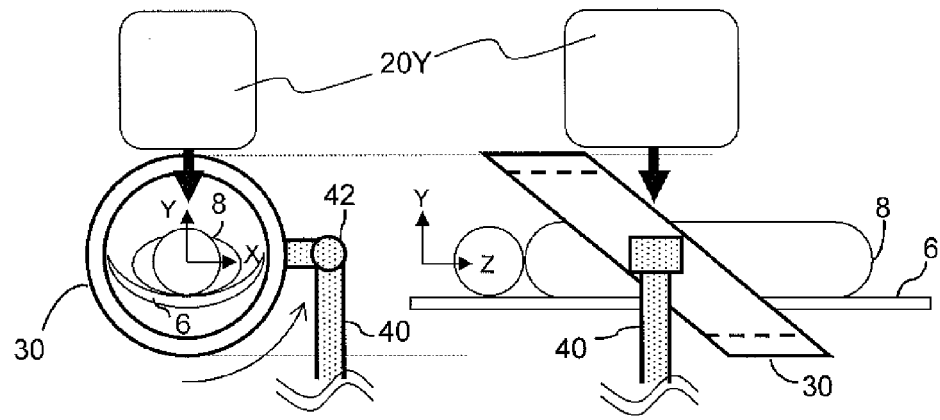

Fig.16
(a) 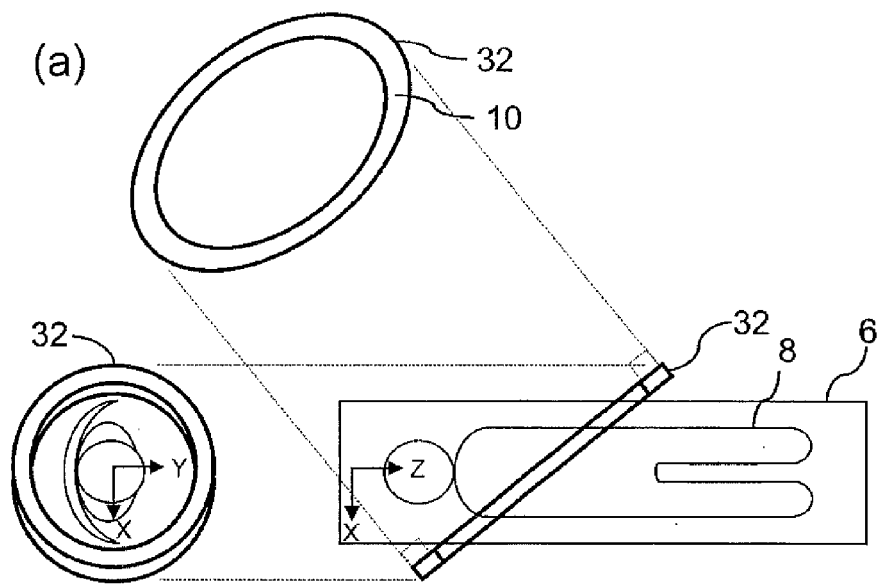
(b) 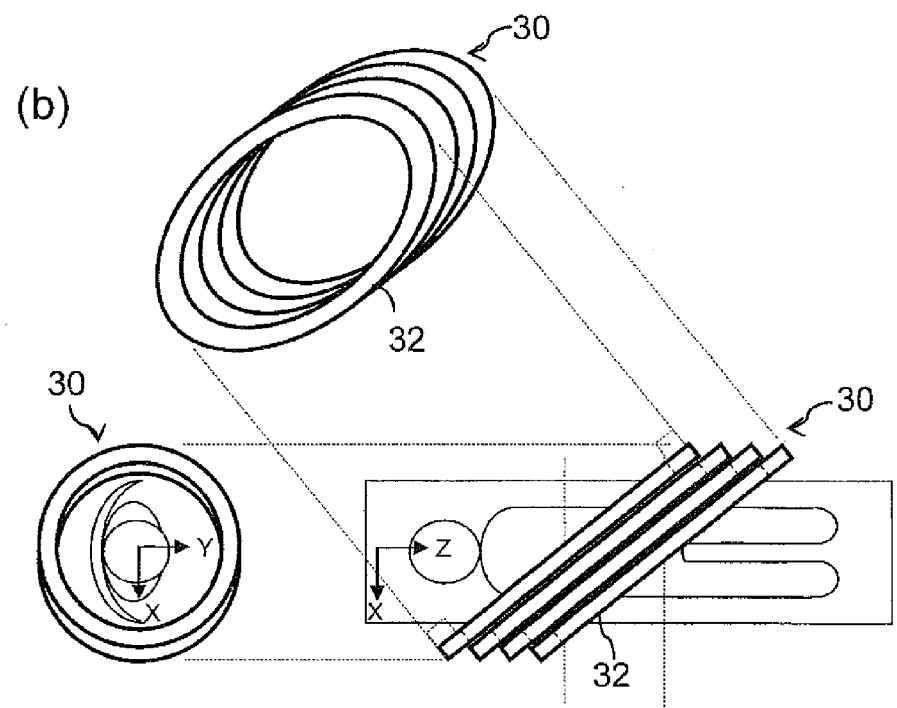

Fig.23
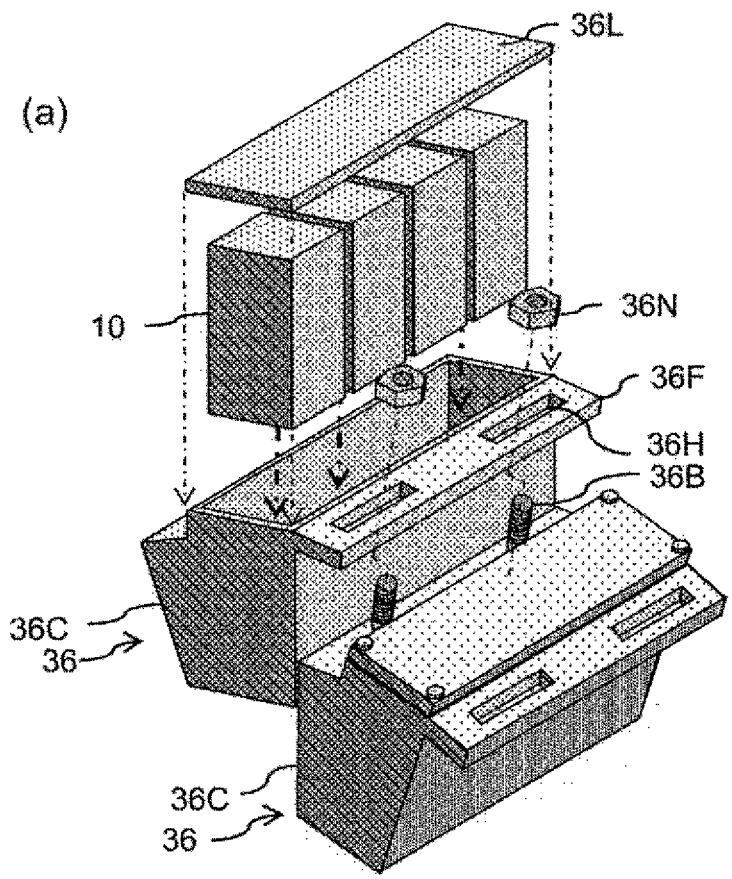
(a)
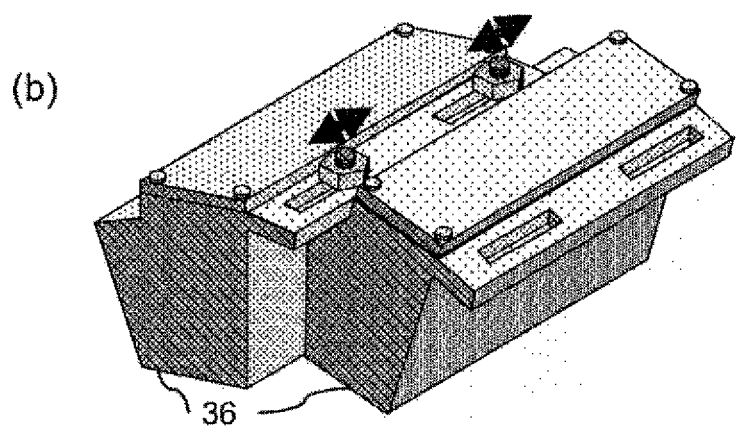
(b)

INCLINED PET DEVICE AND PET COMBINED DEVICE

TECHNICAL FIELD

The present invention relates to an inclined PET device and a PET combined device, and more particularly to an inclined PET device and a PET combined device which are suitable for combination with a radiation cancer treatment device.

BACKGROUND ART

Positron emission tomography (PET), which has been attracting attention as being effective for early diagnosis of cancer, is a test method of administering compounds labeled with a tiny amount of positron emitting radionuclides and detecting annihilation radiations emitted from inside the body, thereby imaging metabolic functions such as sugar metabolism to examine the presence or absence and the degree of diseases. PET devices for practicing such a method have been put to practical use.

The principle of PET is as follows: A positron emitted from a positron emitting radionuclide by positron decay annihilates with an adjacent electron to produce a pair of 511-keV annihilation radiations, which are measured by a pair of radiation detectors according to the principle of coincidence counting. As a result, the position where the nuclide exists can be located to fall on a line segment (line of response) connecting the pair of detectors. An axis extending from the head to the feet of a patient who is a subject to be examined will be defined as a body axis. The distribution of nuclides on a plane intersecting perpendicularly with the body axis is determined by two-dimensional image reconstruction from data on lines of response measured in various directions on the plane.

To increase the sensitivity of a PET device, as illustrated in FIG. 1, a detector ring 12 of cylindrical shape upon which a large number of PET detectors 10 are disposed in a circumferential direction and an axial direction needs to be disposed in a tunnel-like configuration to increase the measurement solid angle, and the distribution of nuclides in the tunnel needs to be determined by three-dimensional image reconstruction. The long tunnel-like patient port, however, increases the psychological stress of the patient 8 on the bed 6 under examination, and interferes with external access to the patient 8 (for example, the irradiation of an affected area of the patient 8 with a radiation beam for cancer treatment which is a main purpose of the present invention). Here, the detector ring 12 mostly has a perfect circular shape. The PET detectors 10 are stacked in a direction perpendicular to the sections of the detector ring 12.

Under the circumstances, the applicants have proposed an open PET device (also referred to as OpenPET) which includes, as illustrated in FIG. 2, a plurality (two, in FIG. 2) of split detector rings 12A and 12B spaced apart in the direction of the body axis and has a physically opened field of view (also referred to as an open field of view) (Patent Literature 1).

The open PET device enables PET diagnosis during treatment and whole-body simultaneous imaging which have not been possible by conventional PET devices. Applications to real-time PET/CT are also possible. Specifically, a treatment can be administered to the open field of view through a gap 12C between the detector rings 12A and 12B. Take a radiation cancer treatment for example. The open PET device can check the cancer position during irradiation with a radiation treatment beam, or visualize the irradiation field of the radiation treatment beam in real time. However, since the detector ring is divided into a plurality of rings and the detector rings need to cover both ends of the irradiation field, the number of detectors increases and the configuration becomes complicated. There is also a problem of limited access directions.

FIG. 3 shows an example of a heavy particle beam, proton beam, or other particle beam cancer treatment device as an example of a device that uses radiations for cancer treatment. This device includes two ports such as a horizontal irradiation port 20X and a vertical irradiation port 20Y. Some devices are single field irradiation devices which include only a horizontal irradiation port or a vertical irradiation port. The irradiation port(s) is/are not always fixed. Some devices include a rotating gantry which is configured to rotate about a patient 8. The rotating gantry type is predominant of proton beam cancer treatment devices in particular. As shown in the diagram, the axis along a horizontal irradiation treatment beam 22X will be defined as X-axis, the axis along a vertical irradiation treatment beam 22Y will be defined as Y-axis, and an axis orthogonal to the Y- and X-axes will be defined as Z-axis. The Z-axis usually coincides with an axis in the direction of the body axis of the patient 8.

In such a particle beam therapy irradiation device, PET measurement during irradiation is needed to check an irradiation field 24 in the body of the patient 8.

As a method for combining a heavy particle irradiation device with PET, Non-Patent Literature 1 describes that the detector ring 12 is inclined to preserve an open space having a width C as shown in FIG. 4. As shown to the upper left of FIG. 4, the detector ring 12 has a perfect circular shape. The PET detectors 10 are stacked in a direction perpendicular to the sections of the detector ring 12. The internal space of the detector ring thus has an elliptical shape when viewed in a direction perpendicular to the Z-axis (the left of the diagram).

CITATION LIST

Patent Literatures

Patent Literature 1: WO 2008/129666
Patent Literature 2: Japanese Patent Application Laid-Open No. 2011-69636

Non-Patent Literature

Non-Patent Literature 1: P. Crespo et al., "On the detector arrangement for in-beam PET for hadron therapy monitoring," Phys. Med. Biol., 51 (2006), 2143-2163

SUMMARY OF THE INVENTION

Problem to be Solved by the Invention

However, to preserve the sufficient open space width C in Non-Patent Literature 1, the detector ring 12 needs to be increased in diameter. This increases the size of the device and the number of PET detectors to use, with an increase in device cost. As the detector ring 12 increases in diameter, the spatial resolution drops due to angular deviations.

For combination with the particle beam therapy, the irradiation port is desired to be brought as close to the patient as possible to suppress spreading of the treatment beam. However, as shown in FIG. 4, the detector ring 12 interferes with bringing the irradiation port (in FIG. 4, the horizontal irradiation port 20X) close to the patient 8. Note that FIG. 4 shows an example of horizontal irradiation. In the method of Non-Patent Literature 1, the orientation of the detector ring 12 cannot be changed according to an arbitrary irradiation direction. There has thus been a problem that the method cannot be used for bilateral irradiations including horizontal irradiation and vertical irradiation or a rotating gantry.

In Patent Literature 1 and Non-Patent Literature 1, the PET detectors are stacked in a direction perpendicular to the sections of the detector ring. Patent Literature 2 describes that PET detectors are disposed and stacked in a direction parallel to the long axis of the bed as with the present invention. However, such a disposition is intended so that the detectors will not obstruct the line of sight of the patient. Unlike Non-Patent Literature 1, no consideration is given to the formation of an open space that passes through the bed in a direction perpendicular to the long axis thereof in order to enable access to the patient.

The present invention has been achieved to solve the foregoing conventional problems. It is thus an object thereof to preserve an open space that is intended to enable access to a subject to be examined and passes through a bed in a direction perpendicular to the long axis thereof, miniaturize the detector ring and therefore the device, and reduce the number of PET detectors for reduced device cost.

Means for Solving the Problem

A principle of the present invention will be described below.

A PET device according to the present invention has a detector arrangement shaped like a circular cylinder that is cut by two planes inclined with respect to the sections of the circular cylinder. As a conventional example, as shown in FIG. 5(a), the PET detectors 10 are stacked in a direction perpendicular to the sections of the detector ring 12. For such a case, the inner diameter D and the width W of the detector ring 12 for preserving an open space width of C with respect to the bed 6 having a width of B are calculated. In the present invention, as shown in FIG. 5(b), the detector ring 30 has a minimum size for the bed 6 to pass through, or D=B, where D is the inner diameter of the detector ring 30 when seen in a direction perpendicular to the center axis, and W is the width. Then, D and W for preserving the open space width of C are calculated.

FIG. 6 shows the calculation results. With the bed width B=60 cm and the open space width C=20 cm, the number of PET detectors to use and the solid angle (relative sensitivity) at the center point of the device are calculated to make a comparison between the present invention and the conventional example. Here, each PET detector is assumed to have a size of 5 cm×5 cm in area. As a result, it was found that the present invention can achieve a higher sensitivity with a smaller number of detectors than heretofore. FIG. 7(a) shows device parameters of the conventional example when the number of detectors is 200 in FIG. 6. FIG. 7(b) shows device parameters of the example of the present invention. The major radius a of the sections of the detector ring 30 was calculated by using a geometric relationship shown in FIG. 8.

As seen above, since the present invention can achieve a higher sensitivity with a smaller number of detectors, the number of detectors can be reduced for cost reduction.

The present invention has been achieved based on such findings, and solves the foregoing problems by the provision of an inclined PET device including a detector ring upon which a plurality of PET detectors are disposed, a cut plane of the detector ring being inclined not to intersect perpendicularly with a long axis of a bed that carries a subject to be examined, an open space being formed that is intended to enable access to the subject to be examined and passes through the bed in a direction perpendicular to the long axis thereof, wherein the respective PET detectors are disposed and stacked in a direction parallel to the long axis of the bed.

Here, the open space may be disposed according to a direction of the access to the subject to be examined.

Moreover, the detector ring may be configured to be rotatable according to the direction of the access to the subject to be examined.

Moreover, the detector ring may be configured to be movable according to a position of the access to the subject to be examined.

Moreover, the detector ring may be rotated according to a horizontal rotation of the bed.

Moreover, the detector ring may be supported by a robot arm.

Moreover, the detector ring may be constituted by stacking unit rings in the direction parallel to the long axis of the bed, the PET detectors being disposed upon the unit rings in an elliptical configuration or polygonal configuration.

Moreover, the unit rings may be disposed stepwise.

Moreover, the cut plane of the detector ring may be configured to be rotatable to a position perpendicular to the long axis of the bed.

Moreover, the unit rings each may be configured to be capable of parallel movement to a mutually coincident position.

Moreover, the unit rings each may be configured to be capable of parallel movement in synchronization with a rotation of the unit rings.

Moreover, detector units upon which a plurality of the PET detectors are disposed in a direction of the long axis of the bed may be shifted little by little in the direction of the long axis of the bed so that the respective PET detectors are disposed and stacked in the direction parallel to the long axis of the bed.

Moreover, amounts of shift of the detector units in the direction of the long axis of the bed may trace a sine wave on a drawing where the detector ring is developed on a plane.

Moreover, the amounts of shift of the detector units may be configured to be variable.

Moreover, main axes of the respective PET detectors may be inclined according to the amounts of shift of the detector units so that the main axes are directed to a center point of the detector ring.

The present invention also provides a PET combined device including the inclined PET device described above and a second device that performs a treatment or an examination in the open space of the inclined PET device.

Here, the second device may be a radiation therapy device, a particle beam therapy device, or an X-ray transmission device.

Moreover, the inclined PET device and the second device may be integrally moved or rotated without interference with each other.

Moreover, at least part of the second device may be supported by the detector ring of the inclined PET device.

Effect of the Invention

According to the present invention, the detector ring can be miniaturized to miniaturize the device. The number of PET detectors can also be reduced to reduce the device cost.

BRIEF DESCRIPTION OF THE DRAWINGS

FIG. 5 is a diagram for describing the principle of the present invention;

FIG. 7 is a diagram similarly showing an example of device parameters with the number of detectors of 200 in FIG. 6;

FIG. 12 is a diagram showing a fourth embodiment of the same;

FIG. 15 is a diagram showing a seventh embodiment of the same;

FIG. 16 is a diagram showing an example of a method for disposing PET detectors;

FIG. 23 is a diagram showing an example of a specific mechanism for implementing the modification of FIG. 21;

BEST MODE FOR CARRYING OUT THE INVENTION

Hereinafter, embodiments of the present invention will be described in detail with reference to the drawings.

Figure 9:
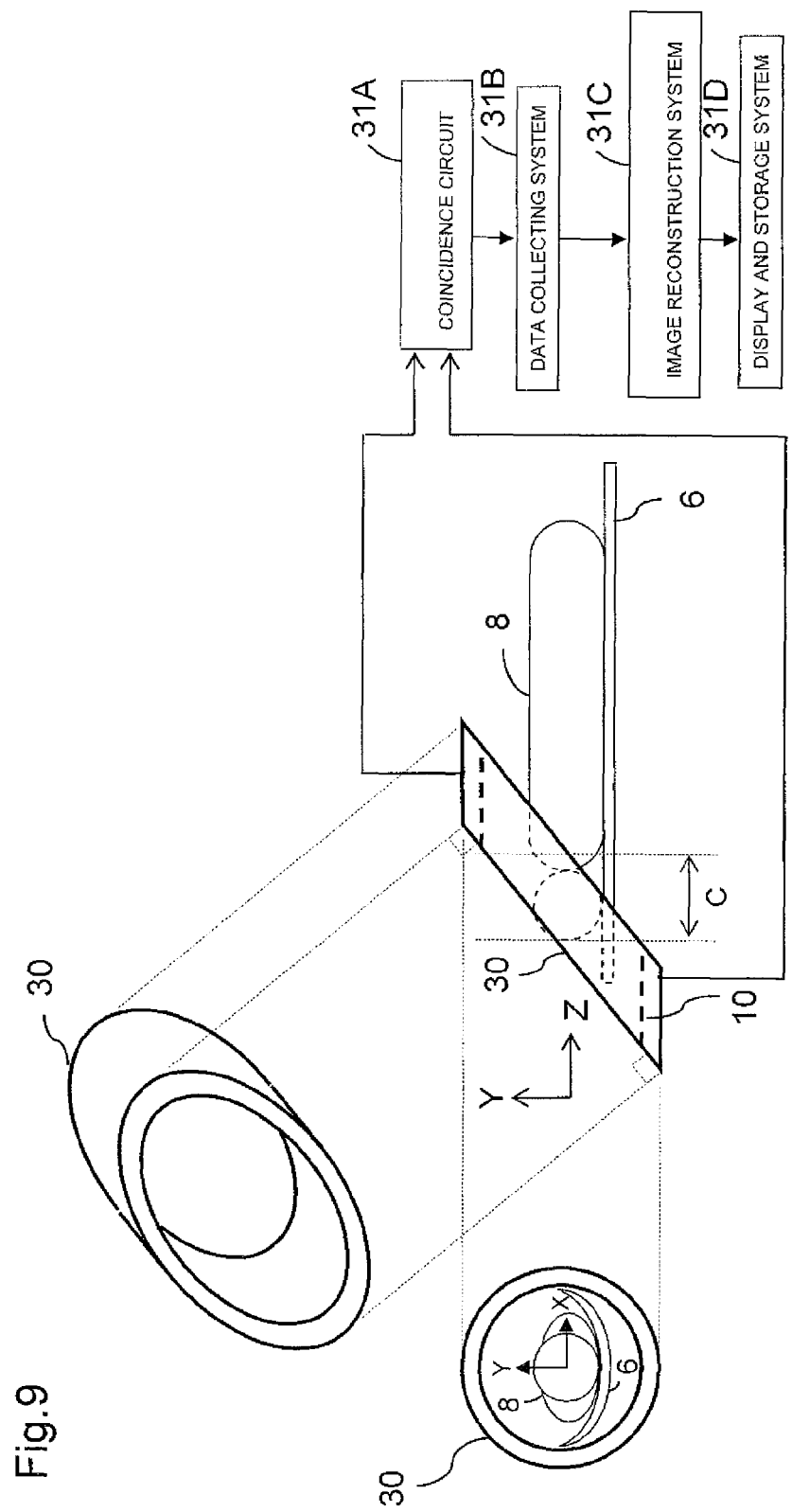
FIG. 9 is a diagram showing a first embodiment of the present invention.

As shown in FIG. 9, a first embodiment of the present invention provides an inclined PET device in which a detector ring 30 upon which a plurality of PET detectors 10 are circumferentially disposed is inclined with respect to the long axis (in the diagram, Z-axis) of a bed 6 of a patient 8 who is a subject to be examined, whereby an open space having a width C is formed that is intended to enable access to the patient 8 and passes through the bed 6 in a direction perpendicular to the long axis thereof (in the diagram, vertical direction). The respective PET detectors 10 are disposed and stacked in a horizontal direction parallel to the long axis of the bed. For example, the width C of the open space is greater than or equal to a width of a treatment beam.

Here, the PET detectors 10 constituting the detector ring 30 are stacked in a direction not perpendicular to the sections of the same. The stacking direction of the PET detectors 10 is configured to be close to the Z-axis or the long axis of the bed 6.

In other words, the detector ring 30 has a shape such that a detector ring 12 of perfect circular cylindrical shape like the conventional example is obliquely cut by two parallel planes not perpendicular to the axis. The detector ring 30 has a perfect circular cross section when seen in the Z-axis direction as shown to the left of the diagram, and an elliptical cross section when seen in a direction perpendicular to the sections of the detector ring 30 as shown to the upper left of the diagram.

In the present embodiment, single event data on annihilation radiations detected by the PET detectors 10 is converted by a coincidence circuit 31A into coincidence data for identifying lines of response, and stored in a data collecting system 31B in succession. After the accumulation of the measurement data for a certain time, an image reconstruction system 31C performs image reconstruction calculations to display or store an image of the irradiation field on/in a display and storage system 31D.

Figure 1:
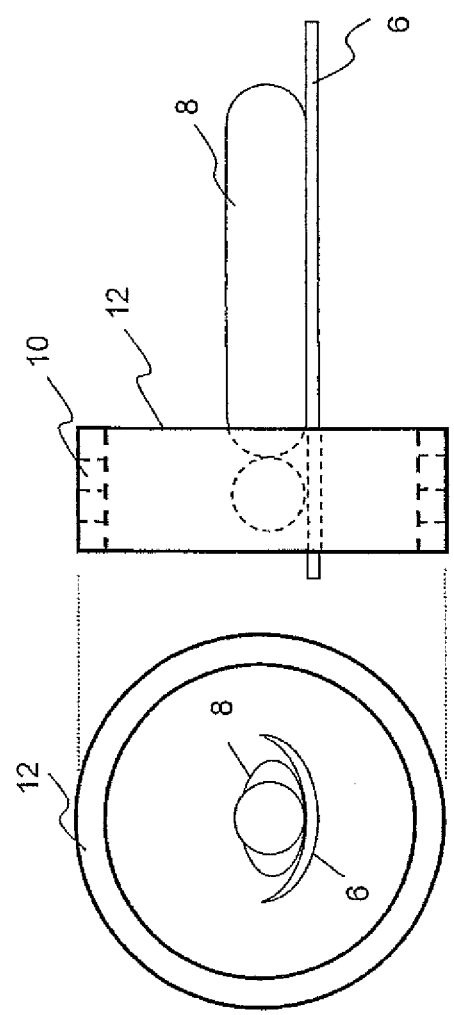
FIG. 1 is a diagram showing an example of a conventional PET device.
Figure 2:
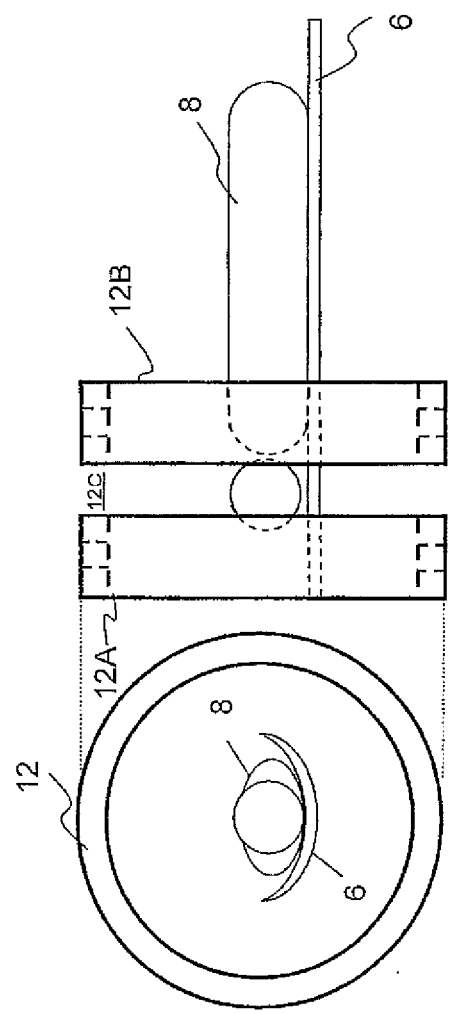
FIG. 2 is a diagram similarly showing an example of an open PET device.
Figure 3:
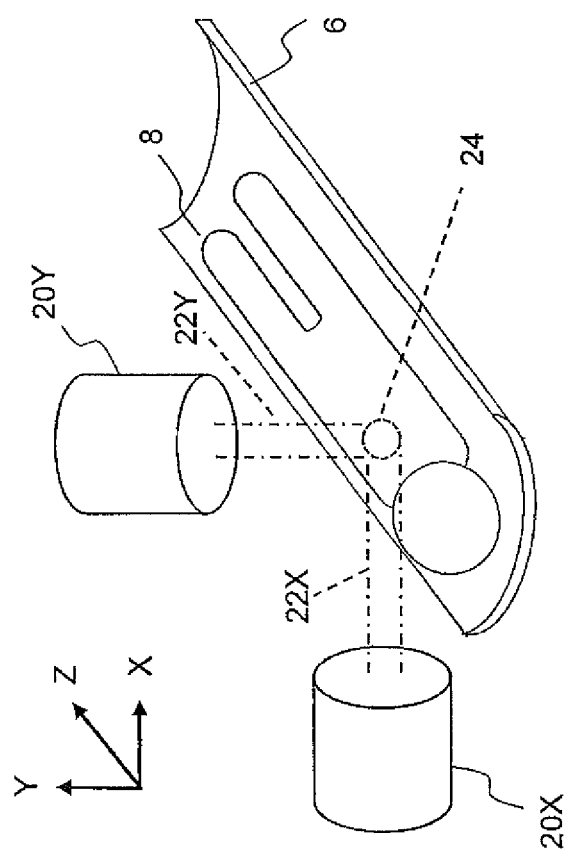
FIG. 3 is a diagram schematically showing an example of a conventional particle beam irradiation device.
Figure 4:
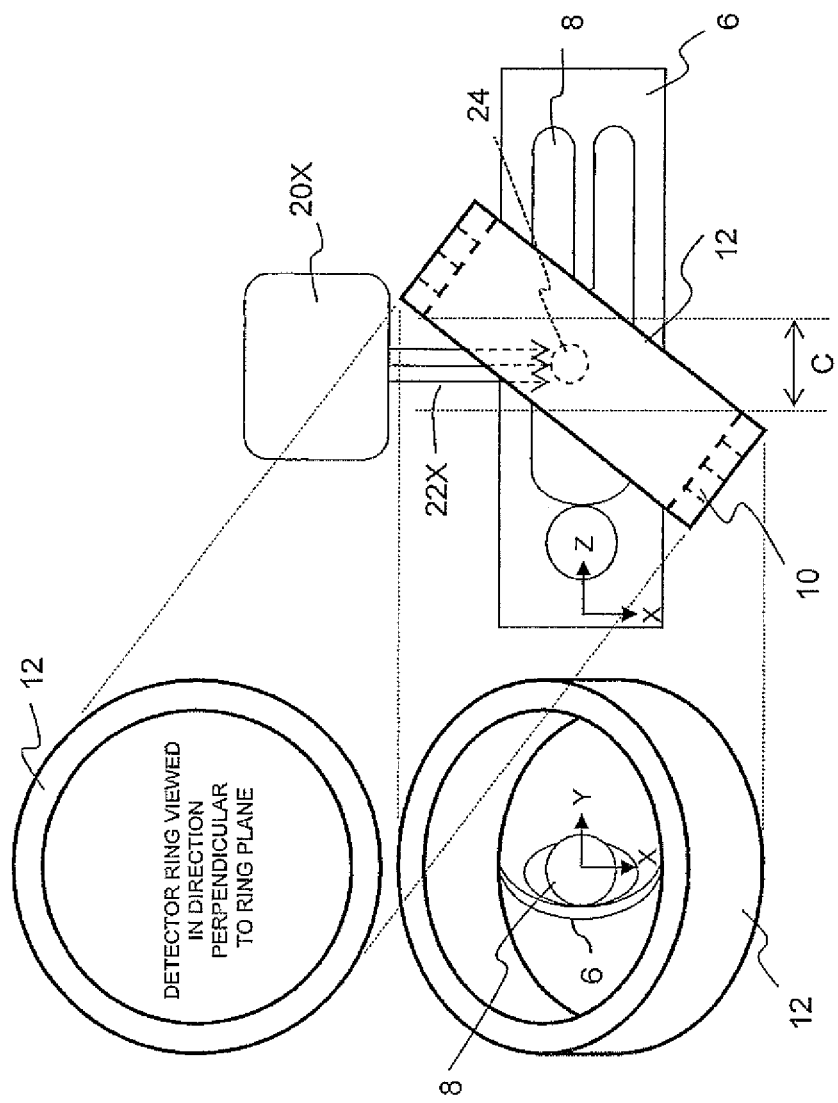
FIG. 4 is a diagram showing an example proposed in Non-Patent Literature 1, where a heavy particle beam irradiation device is combined with a PET.
Figure 6:
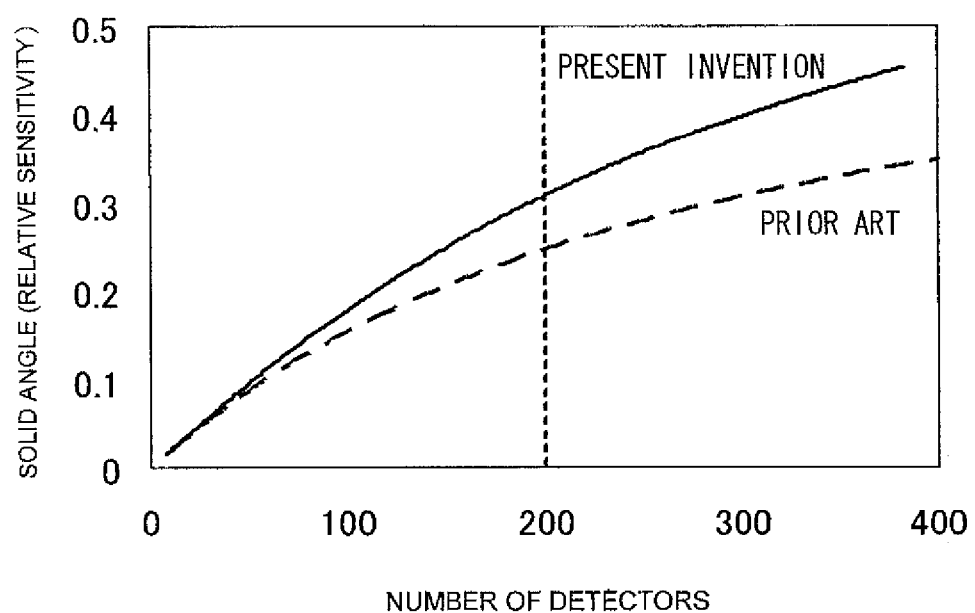
FIG. 6 is a diagram showing a simulation result of the same.
Figure 8:
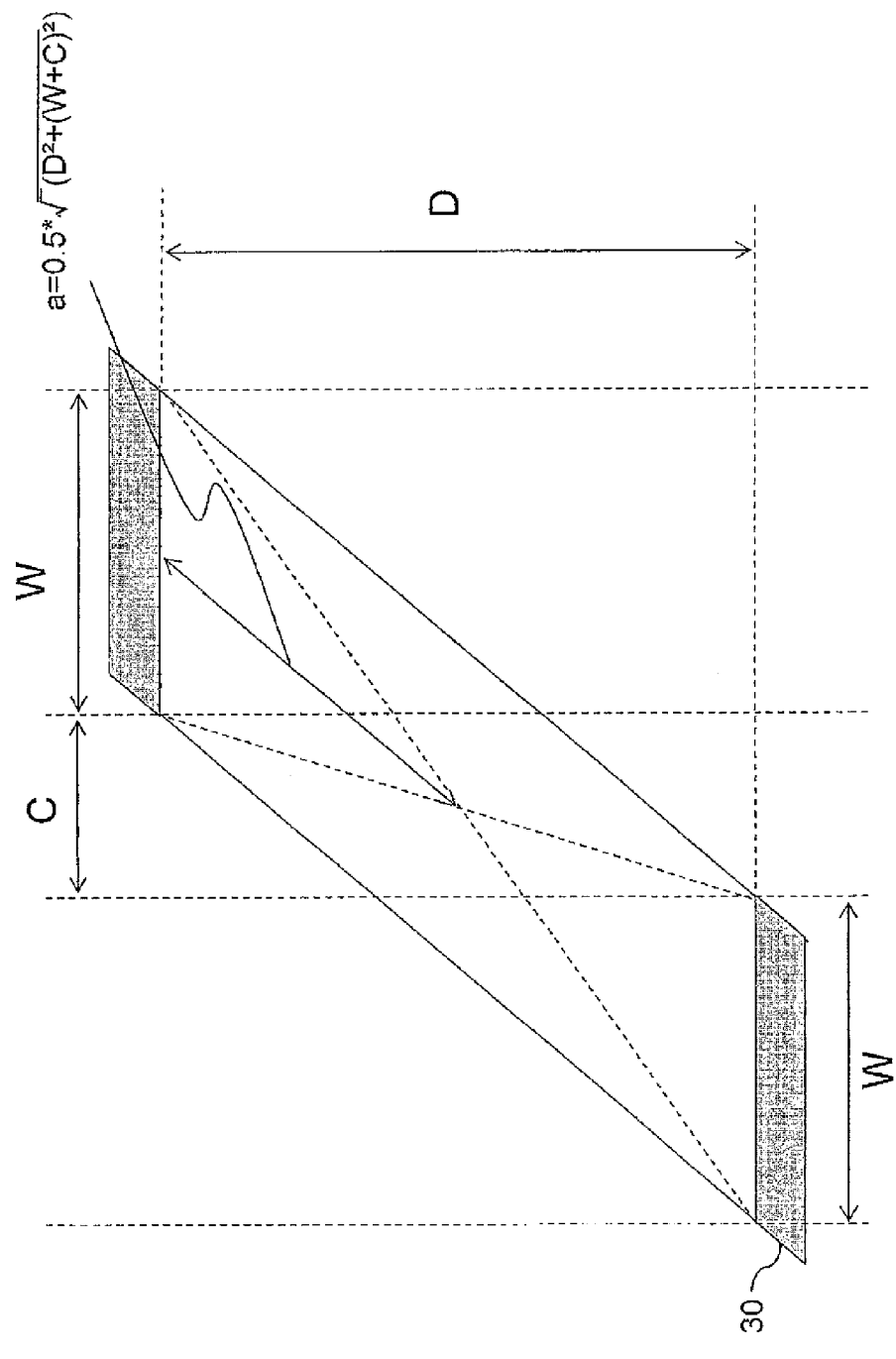
FIG. 8 is a diagram similarly showing a geometric relationship used for calculation.
Figure 10:
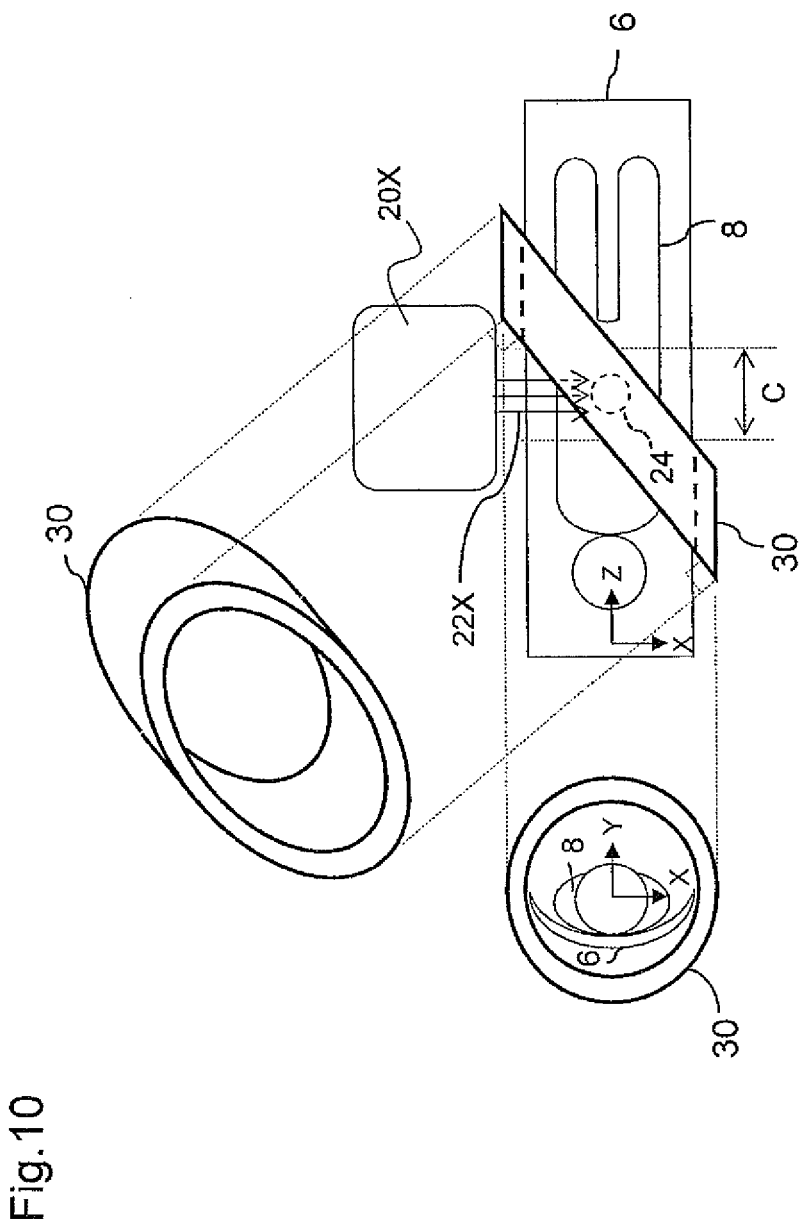
FIG. 10 is a diagram showing a second embodiment of the same.

FIG. 10 shows a second embodiment of the present invention where a horizontal irradiation particle beam therapy device having a horizontal irradiation port 20X is combined with the first embodiment. As compared to FIG. 4 where the horizontal irradiation port 20X is combined with a conventional PET device, the horizontal irradiation port 20X can be brought closer to the irradiation field 24 of the patient 8 to suppress the spreading of the treatment beam 22X.

In use, for example, the irradiation field 24 is irradiated with the treatment beam 22X from the horizontal irradiation port 20X as in Non-Patent Literature 1. During, before, or after the irradiation, the signals obtained by the detection ring 30 can be used to obtain a PET image of the irradiation field 24 by the same technique as in the first embodiment.

Figure 11:
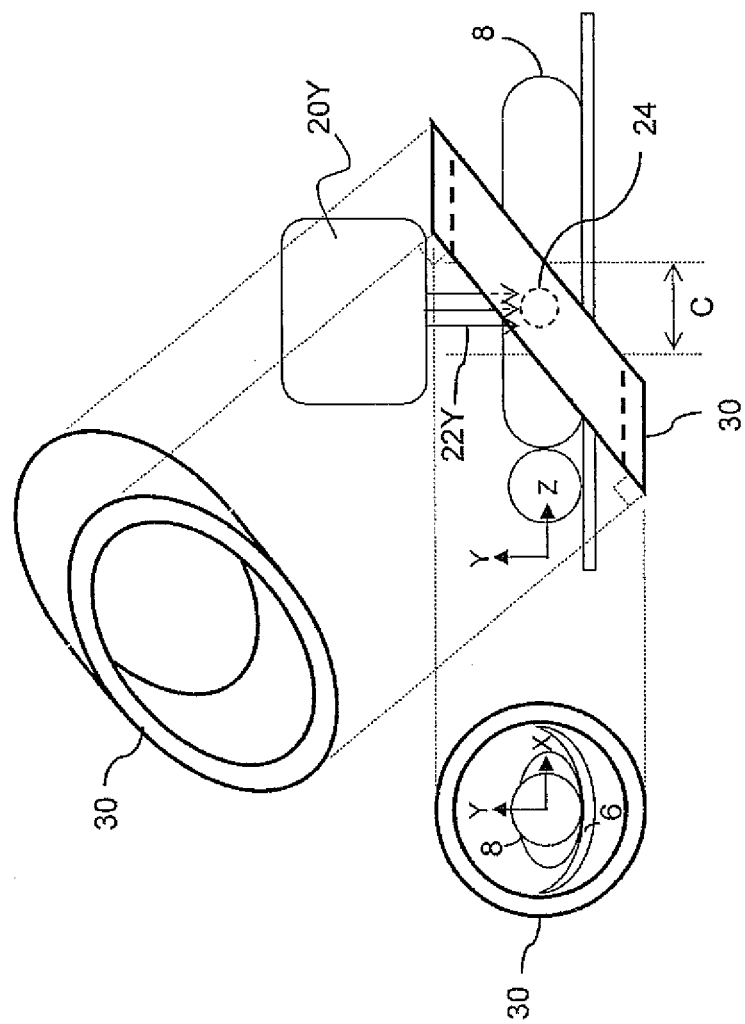
FIG. 11 is a diagram showing a third embodiment of the same.

FIG. 11 shows a third embodiment of the present invention where a vertical irradiation particle beam therapy device having a vertical irradiation port 20Y is combined with the first embodiment. According to the present embodiment, the vertical irradiation port 20Y can be brought close to the irradiation field 24 of the patient 8 to suppress the spreading of the treatment beam 22Y.

In use, for example, the irradiation field 24 is irradiated with the treatment beam 22Y from the vertical irradiation port 20Y as in Non-Patent Literature 1. During, before, or after the irradiation, the signals obtained by the detection ring 30 can be used to obtain a PET image of the irradiation field 24 by the same technique as in the first embodiment.

Note that if the detector ring 30 is configured to be rotatable about the Z-axis or an axis near the Z-axis, the horizontal irradiation of FIG. 10 and the vertical irradiation of FIG. 11 and even irradiations at other arbitrary angles can be performed by one device.

FIG. 12 shows a fourth embodiment of the present invention where the detector ring 30 is configured to be capable of parallel movement in the Z-axis direction according to a movement of the irradiation field 24.

The foregoing description has dealt with the cases where the irradiation field 24 lies in the center as shown in FIG. 12(a). However, as in the present embodiment, the position of the detector ring 30 can be changed to deal with the movement of the irradiation field 24. As shown in FIG. 12(b), if the irradiation field 24 moves in the positive direction of the X-axis (downward in the diagram), the detector ring 30 may be shifted in the positive direction of the Z-axis (to the right in the diagram). As shown in FIG. 12(c), if the irradiation field 24 moves in the negative direction of the X-axis, the detector ring 30 may be further rotated 180° about the Z-axis (or on the XZ plane). While FIG. 12 shows an example of horizontal irradiation, vertical irradiation can be similarly handled.

Figure 13:
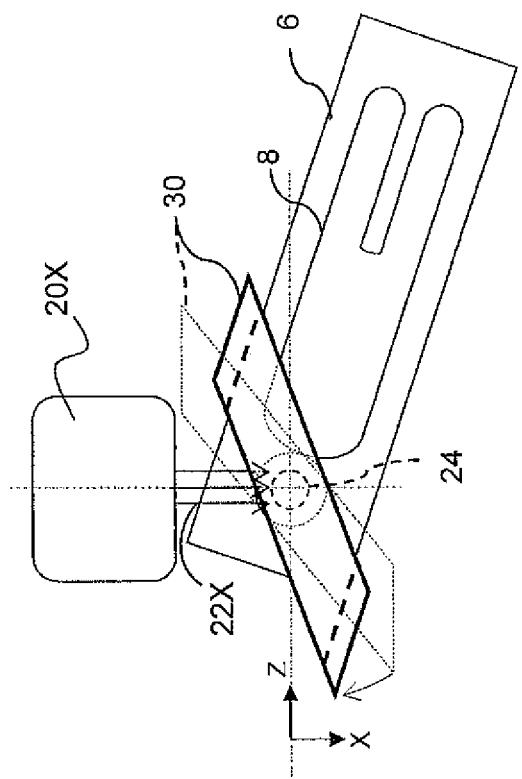
FIG. 13 is a diagram showing a fifth embodiment of the same.

As shown in FIG. 13, non-coplanar irradiation is sometimes performed with the long axis of the bed off the Z-axis, particularly for head irradiation. In such a case, as in a fifth embodiment shown in FIG. 13, the detector ring 30 can be rotated according to the rotation of the bed 6. While FIG. 13 shows an example of horizontal irradiation, vertical irradiation can be similarly handled.

Figure 14:
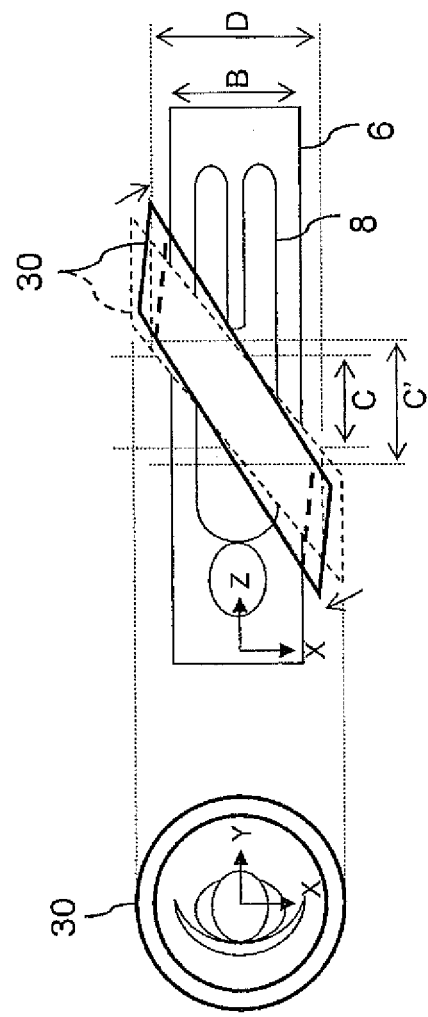
FIG. 14 is a diagram showing a sixth embodiment of the same.

As in a sixth embodiment shown in FIG. 14, the detector ring 30 may be configured to be somewhat greater than the patient bed 6, so that the detector ring 30 can be rotated a little to increase the open space width C. As shown in FIG. 14, if the inner diameter D of the detector ring 30 when seen in a direction perpendicular to the Z-axis is configured to be somewhat greater than the patient bed width B, the detector ring 30 can be rotated clockwise as shown by the arrows to increase the open space width from C to C'.

FIG. 15 shows a seventh embodiment of the present invention where the detector ring 30 is supported by a robot arm 40 so that, for example, (a) horizontal irradiation and (b) vertical irradiation both can be performed. In the diagram, 42 denotes a fulcrum of the robot arm. The present embodiment is also compatible with a rotating gantry.

Next, a method for disposing PET detectors 10 of rectangular solid shape will be described. FIG. 16 shows an example thereof.

Initially, as shown in FIG. 16(a), PET detectors 10 are elliptically disposed on the same plane to form a unit ring 32. Next, as shown in FIG. 16(b), unit rings 32 formed thus are disposed in a stepwise configuration in a direction parallel to the Z-axis to form the detector ring 30. Note that the unit rings 32 need not necessarily be elliptical and may be polygonal in shape.

Figure 17:
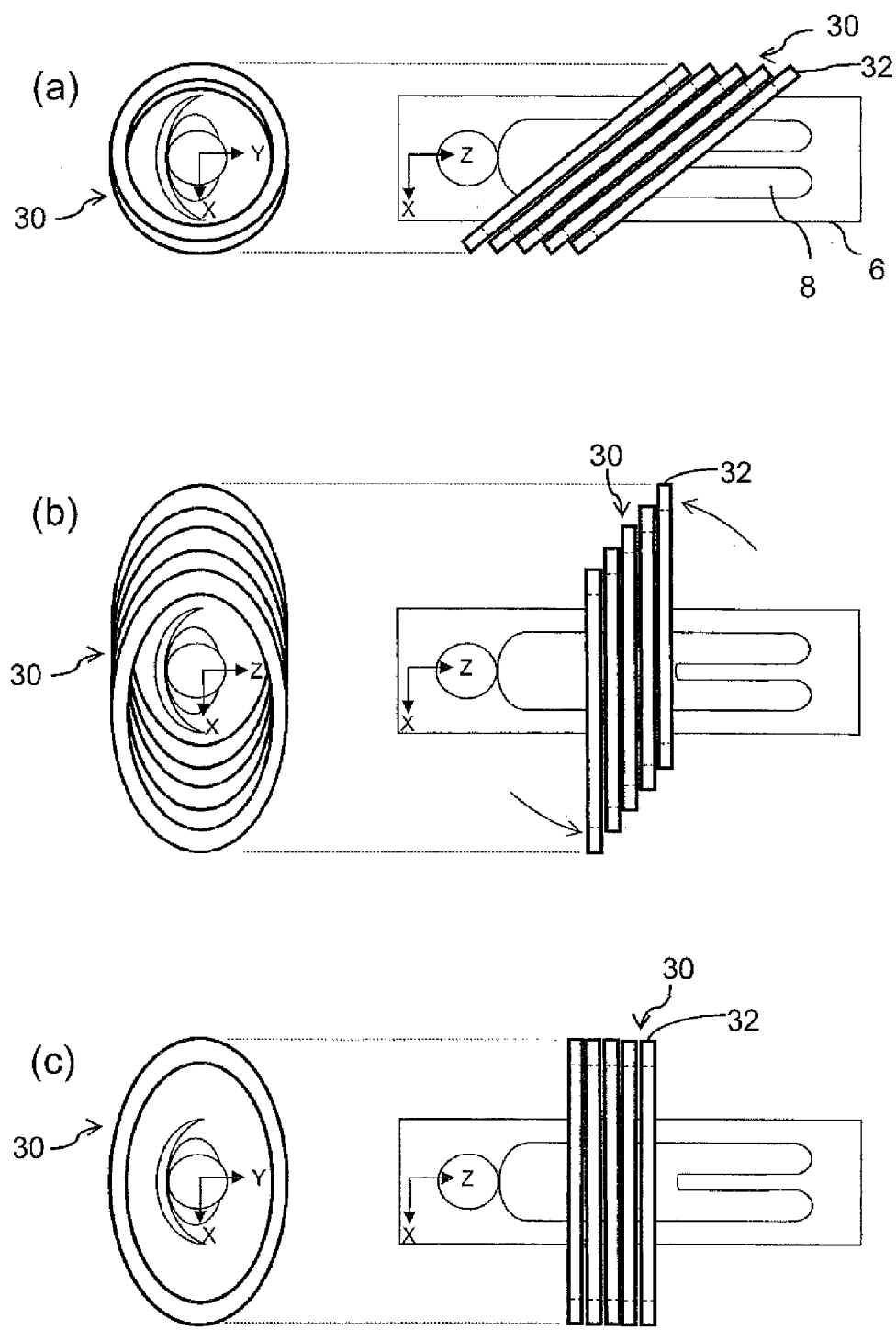
FIG. 17 is a diagram showing a modification of FIG. 16.

Take the case where the open space is not necessary needed like when in an ordinary PET diagnostic use. With the detector ring 30 inclined as in FIG. 17(a), the radiations intersect with the body by a longer distance. This reduces the amount of detectable radiations because of increased radiation absorption by the body. To reduce the degree of absorption of the radiations by the patient's body, as shown in FIG. 17(b), the entire detector ring 30 can be rotated along the XZ plane. This may limit the field of view when measuring a longitudinal imaging object like the patient 8 on the bed 6. Then, as shown in FIG. 17(c), the unit rings 32 can be aligned to widen the field of view.

Figure 18:
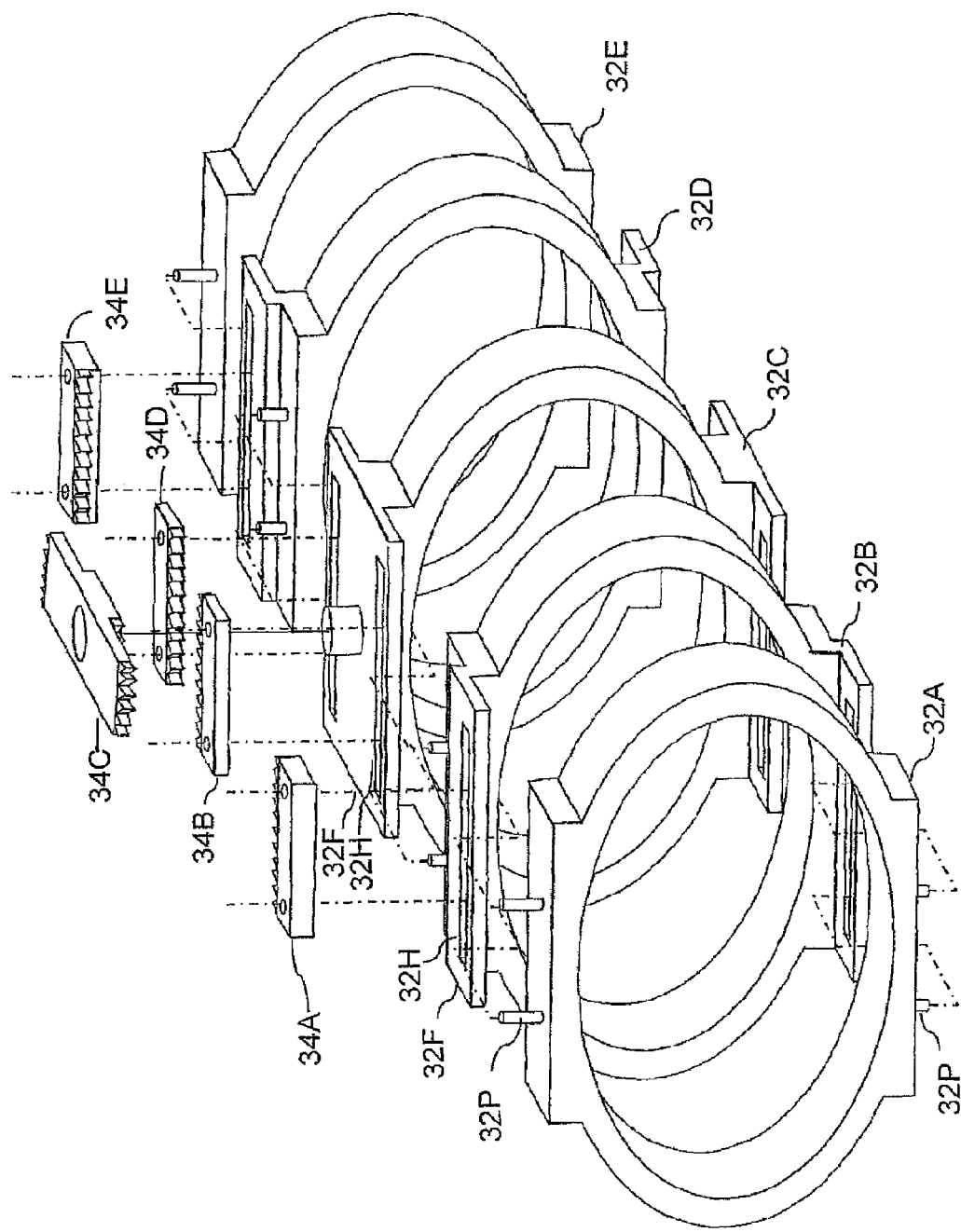
FIG. 18 is an exploded perspective view showing an example of a specific mechanism for implementing the modification of FIG. 17.
Figure 19:
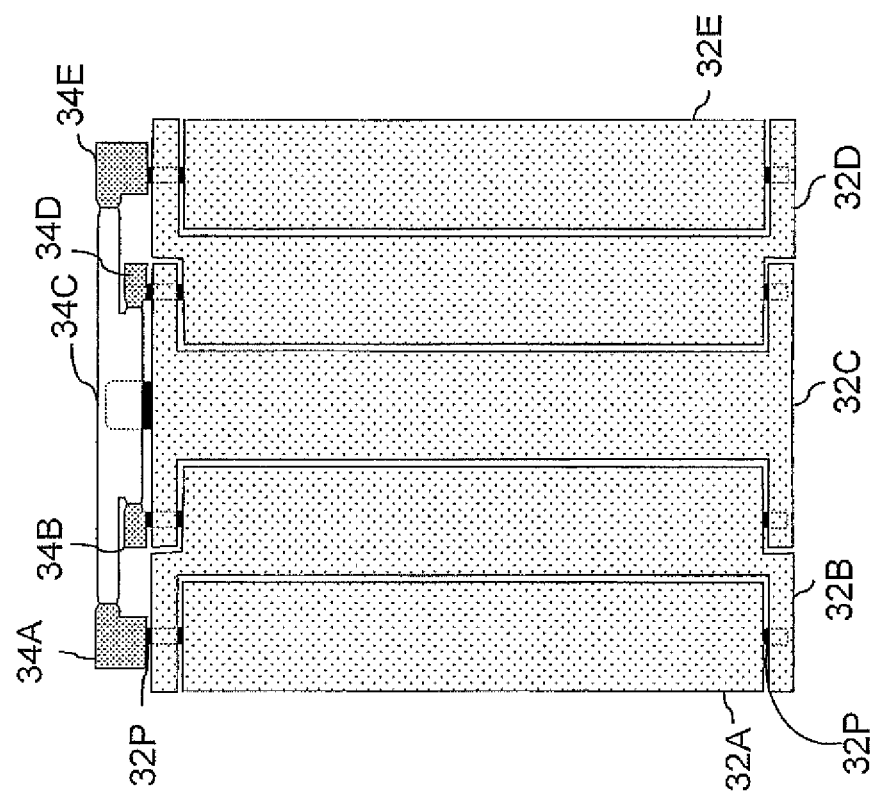
FIG. 19 is a side view of the same.
Figure 20:
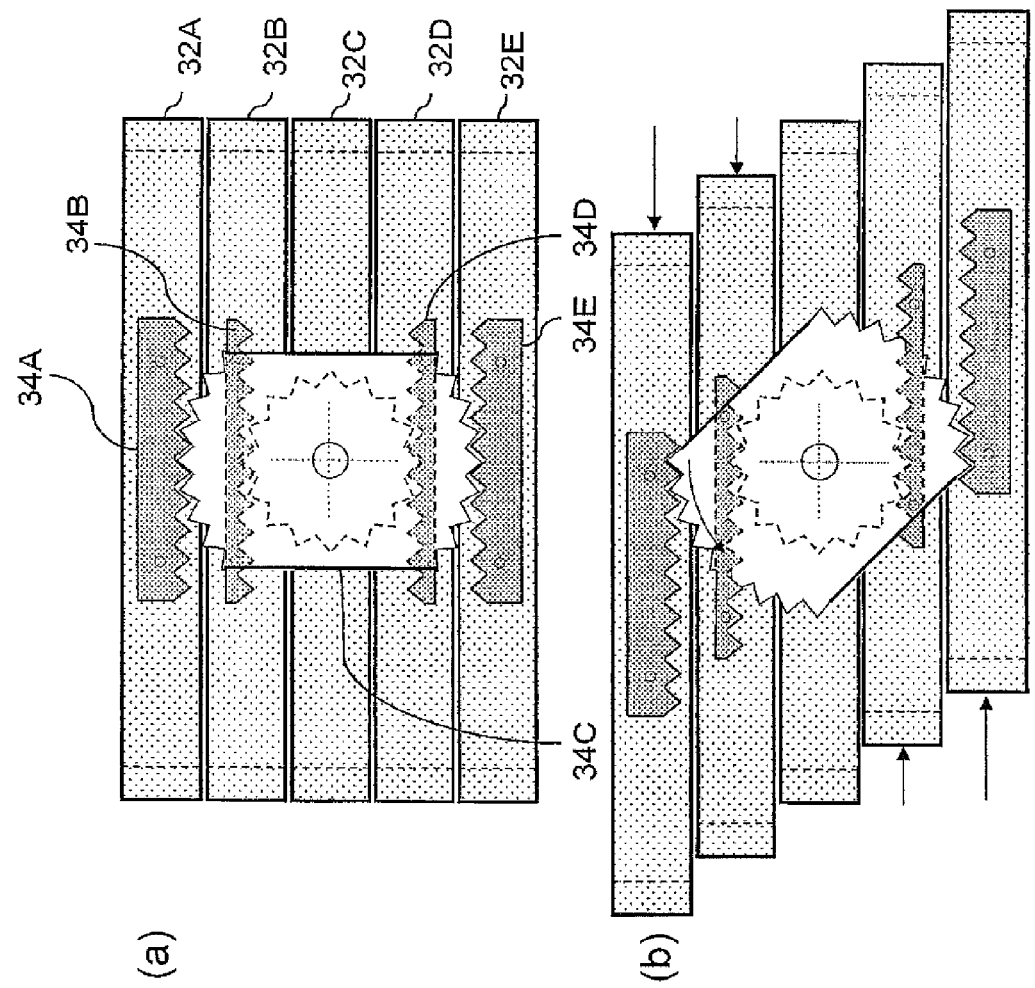
FIG. 20 is a top view of the same.

FIG. 18 (exploded perspective view), FIG. 19 (side view), and FIG. 20 (top view) show an example of a specific mechanism for making the deformation from FIG. 17(b) to FIG. 17(c).

This mechanism includes, for example, two protruded pins 32P which are protruded from both the top and bottom of each of five unit rings 32A to 32E, flanges 32F which have a long hole 32H for pins 32P to be inserted through, and gears 34A to 34E which are intended to make the unit rings 32A to 32E slide at respective constant widths and arranged, for example, on the top of the respective unit rings 32A to 32E.

According to such an example, the rotation of the center gear 34C can move all the unit rings 32A to 32E from the stepwise configuration into the cylindrical configuration in an interlocked manner. The movement may be manually made or electrically powered.

Figure 21:
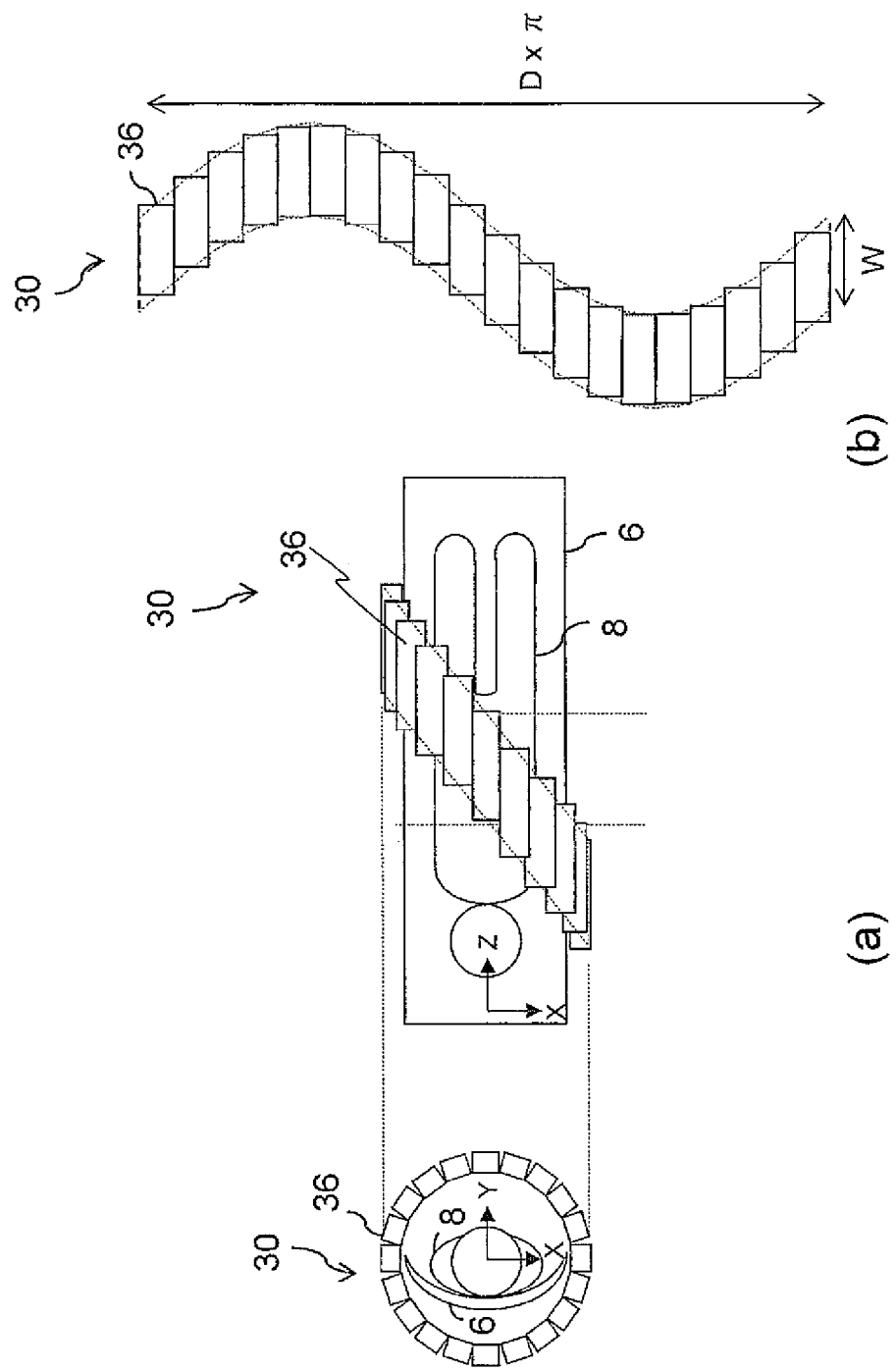
FIG. 21 is a diagram showing another example of the method for disposing PET detectors.

Next, another example of the method for disposing the PET detectors of rectangular solid shape will be described. PET detectors disposed in a row will be referred to as a bucket. As shown in FIG. 21(a), buckets 36 can be shifted little by little in the Z-axis direction to construct the detector ring 30 of the present invention.

As shown in FIG. 21(a), to configure the sections of the detector ring as flat planes, the buckets 36 may be shifted in the Z-axis direction by amounts according to a sine function as in a developed view of the detector ring 30 shown in FIG. 21(b). If typical PET detectors including scintillators of several centimeters in thickness are used, the position discrimination performance of obliquely incident radiations may drop. However, DOI (Depth-of-interaction) detectors capable of the position discrimination of radiations even in the depth direction of the scintillators (see Japanese Patent Application Laid-Open Nos. Hei. 6-337289, Hei. 11-142523, 2004-132930, 2004-279057, 2007-93376, and 2005-43062 and the like) can be used to maintain the position discrimination performance of obliquely incident radiations.

Figure 22:
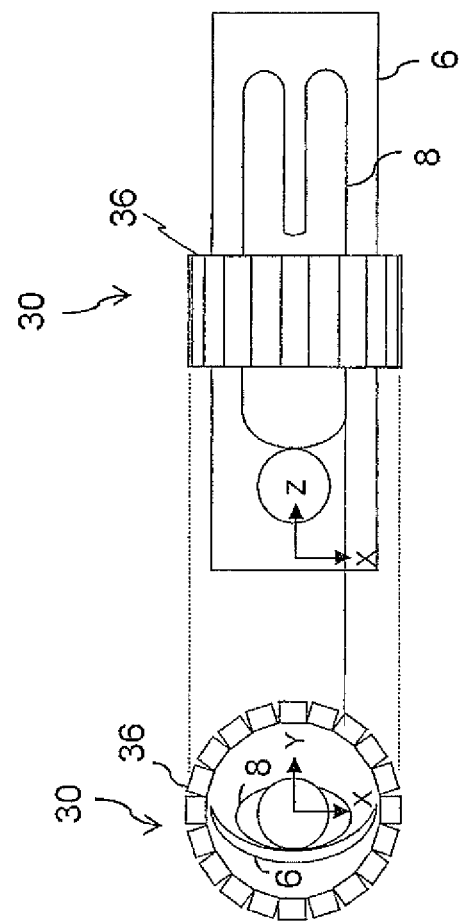
FIG. 22 is a diagram showing a modification of FIG. 21.

The amounts of shift of each of the buckets 36 in the Z-axis direction may be configured to be variable. For an ordinary PET diagnosis where no open space is needed, as in a modification shown in FIG. 22, the PET device may be configured as an ordinary PET device having a cylindrical detector ring without an open space.

FIG. 23 shows an example of a specific mechanism for making the buckets 36 movable. As shown in FIG. 23(a), PET detectors 10 are accommodated in a detector case 36C constituting a bucket 36, and covered with a lid 36L. The detector case 36C has a flange 36F with a long hole 36H, and bolts 36B of an adjoining detector case 36C are passed through the long hole 36H and fixed by nuts 36N. As shown in FIG. 23(b), the buckets 36 can thus be made movable in the longitudinal direction.

Figure 24:
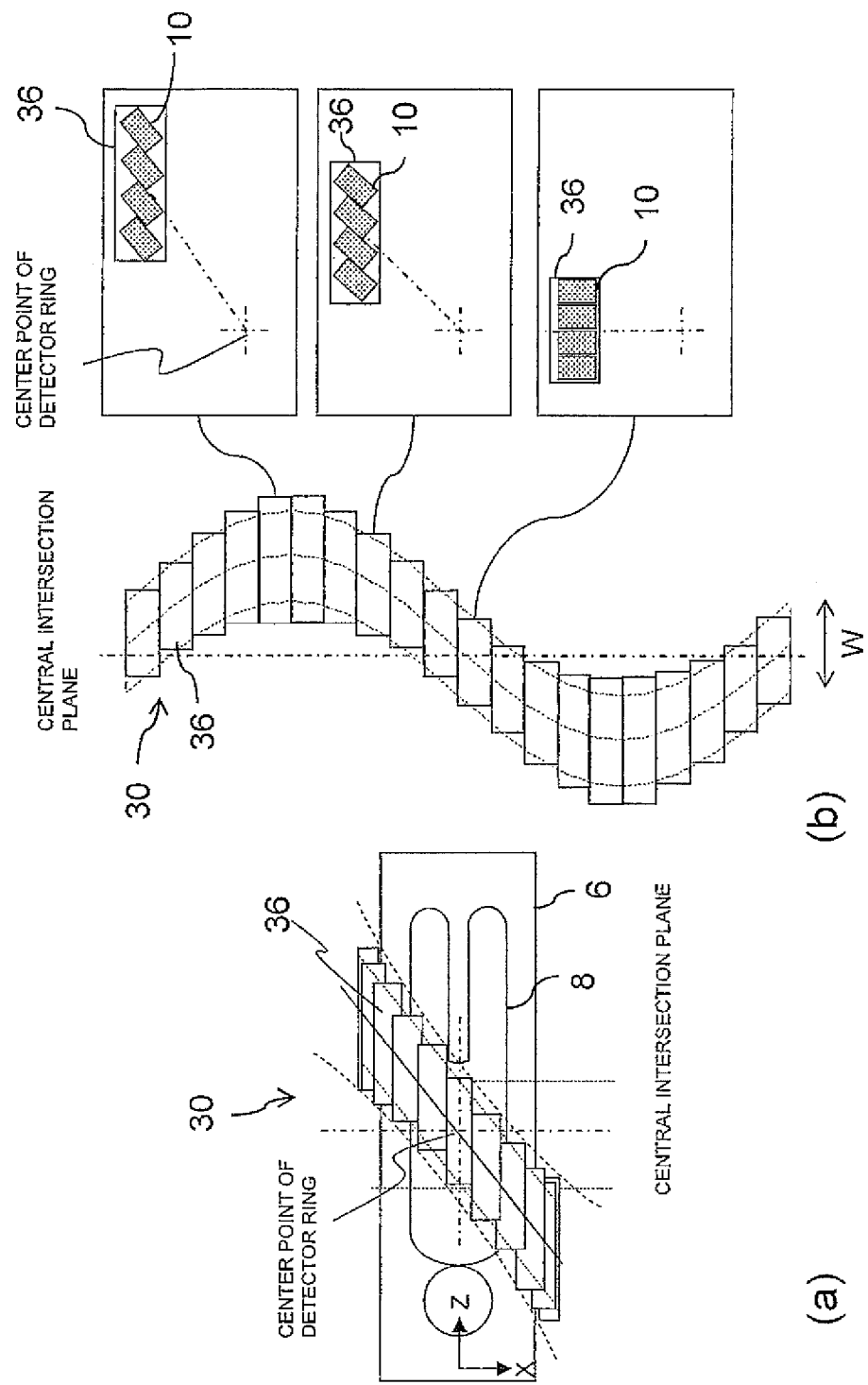
FIG. 24 is a diagram showing another modification of FIG. 21.

Moreover, as in a modification shown in FIG. 24, the main axes of the PET detectors 10 may be inclined according to the positions of the buckets 36 so that the main axes of the PET detectors 10 are directed to the center point of the detector ring 30. As a result, the angles of the radiations incident on the PET detectors can be made close to perpendicular, whereby the position discrimination performance can be maintained despite the use of ordinary PET detectors other than DOI detectors.

The inclination of the main axes of the PET detectors 10 increases the detection width in the Z-axis direction. An elliptical detector ring originally has the problem that the sensitivity drops due to a decrease of the solid angle in the major-axis direction of the ellipse as compared to the minor-axis direction of the ellipse. The inclination of the main axes of the PET detectors 10 can aptly increase the detection width as the direction approaches the long-axis direction, whereby the decrease of the solid angle can be suitably suppressed.

Figure 25:
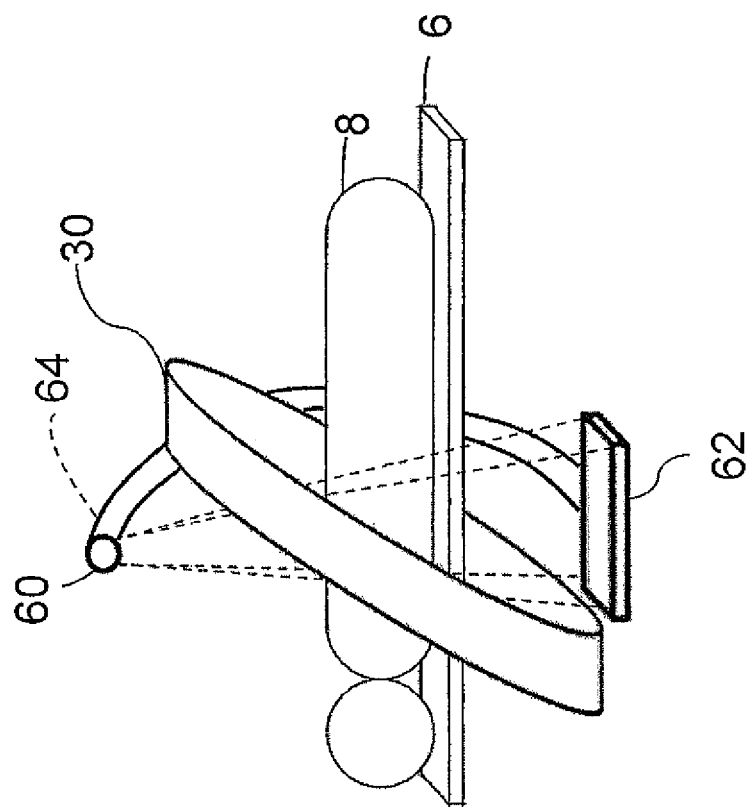
FIG. 25 is a diagram showing an eighth embodiment of the present invention according to a PET combined device.

Next, FIG. 25 shows an eighth embodiment of the present invention according to a PET combined device which combines the PET device according to the present invention and an X-ray transmission device. In the present embodiment, an X-ray source 60 and an X-ray detector 62 independent of the detector ring 30 are disposed by an arm 64 so that the irradiating X-rays pass through the open space. Consequently, for example, a tumor can be imaged by the PET device while the shape of bones and organs around the tumor and the positional relationship of a biopsy needle are checked by an X-ray image for increased accuracy of needle biopsy. Moreover, the entire PET device and X-ray transmission device can be rotated to constitute a PET/CT combined device.

Figure 26:
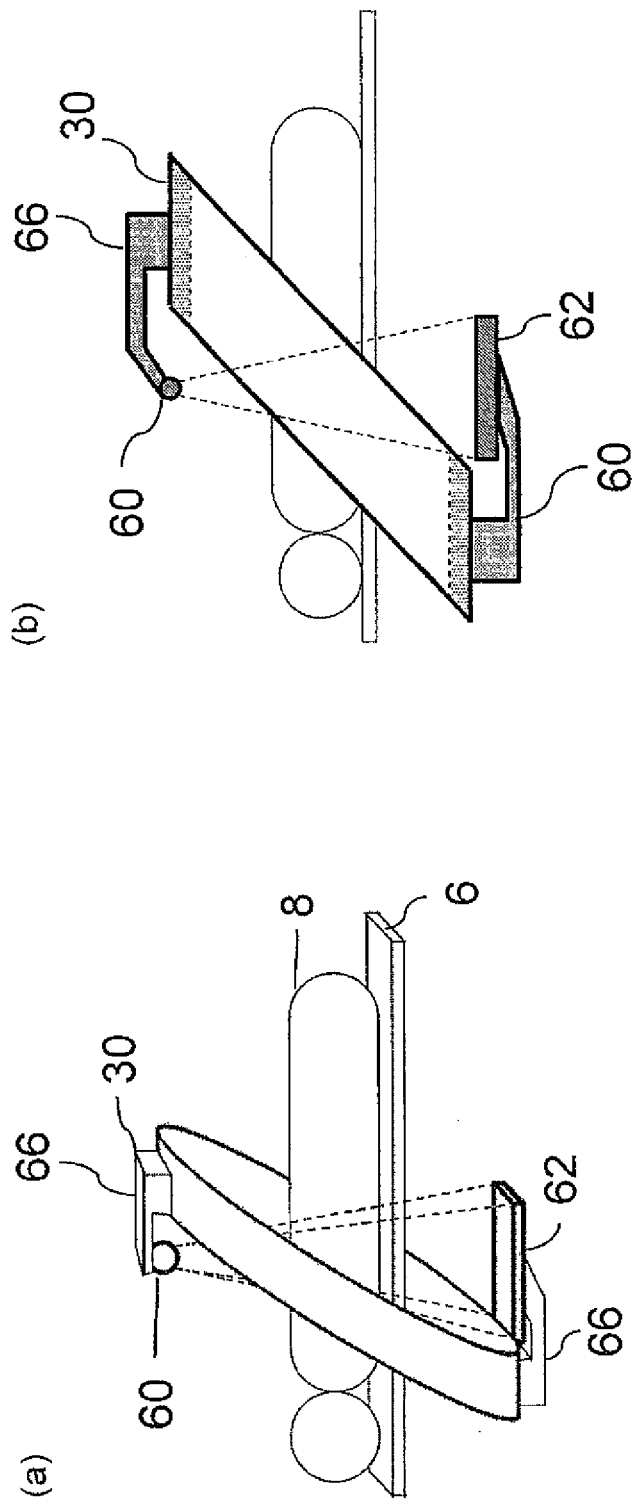
FIG. 26 is a diagram similarly showing a ninth embodiment of the present invention.

FIGS. 26(a) (perspective view) and 26(b) (sectional view) show a ninth embodiment of the present invention where the X-ray source 60 and the X-ray detector 62 are fixed to the detector ring 30 by using holders 66. According to the present embodiment, the arm such as that of the eighth embodiment can be omitted to constitute the PET combined device at low price.

Figure 27:
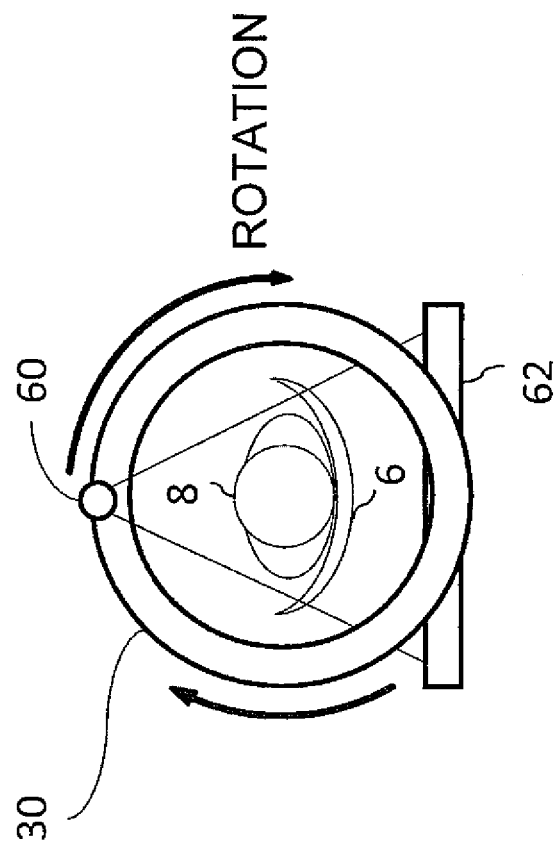
FIG. 27 is a diagram showing a state where the ninth embodiment is rotated.

As shown in FIG. 27, the entirety can be rotated to constitute a simultaneous field-of-view PET/CT combined device.

In the foregoing embodiments, the PET device according to the present invention is combined with a radiation therapy device or an X-ray transmission device. However, the devices to be combined with the PET device are not limited thereto. The PET device may be used singly.

The PET detectors need not necessarily be densely disposed in the circumferential and axial directions of the detector ring. The PET detectors may be spaced apart from each other.

INDUSTRIAL APPLICABILITY

An inclined PET device and a PET combined device suitable for combination with a radiation therapy device and an X-ray transmission device are obtained.

REFERENCE SIGNS LIST

6 . . . Bed
8 . . . Patient (subject to be examined)
10 . . . PET detector
20X, 20Y . . . Irradiation port
22X, 22Y . . . Treatment beam
24 . . . Irradiation field
30 . . . Detector ring
32 . . . Unit ring
36 . . . Bucket
60 . . . X-ray source
62 . . . X-ray detector
64 . . . Arm
66 . . . Holder

The invention claimed is:

1. An inclined PET device comprising:
a detector ring; and
a plurality of PET detectors disposed in the detector ring, edges of the detector ring being inclined at an angle oblique to a vertical axis perpendicular to a long axis of a bed for an examination subject, when viewed in a direction corresponding to a horizontal axis perpendicular to the long axis of the bed;
wherein:
none of the PET detectors on opposite portions of the detector ring on either side of the bed overlap in a direction corresponding to the vertical axis perpendicular to the long axis of the bed, when viewed in the direction corresponding to the horizontal axis perpendicular to the long axis of the bed;
an open space with width for access is formed between the opposite portions of the detector ring on either side of the bed, the open space being formed in the direction corresponding to the vertical axis perpendicular to the long axis of the bed, when viewed in the direction corresponding to the horizontal axis perpendicular to the long axis of the bed, the open space enabling access to the examination subject, and the open space passing through the bed in the direction corresponding to the vertical axis perpendicular to the long axis of the bed, when viewed in the direction corresponding to the horizontal axis perpendicular to the long axis of the bed; and
the respective PET detectors are disposed and stacked in a direction parallel to the long axis of the bed.

2. The inclined PET device according to claim 1, wherein the detector ring is configured to be rotatable according to a direction of the access to the examination subject.

3. The inclined PET device according to claim 1, wherein the detector ring is configured to be movable according to a position of the access to the examination subject.

4. The inclined PET device according to claim 1, wherein the detector ring is configured to be rotated according to a horizontal rotation of the bed.

5. The inclined PET device according to claim 1, further comprising a robot arm, the detector ring being supported by the robot arm.

6. The inclined PET device according to claim 1, wherein the detector ring includes unit rings in which the PET detectors are disposed in an elliptical configuration or a polygonal configuration, the unit rings being stacked in the direction parallel to the long axis of the bed.

7. The inclined PET device according to claim 6, wherein the unit rings are disposed stepwise.

8. The inclined PET device according to claim 6, wherein a cut plane of the detector ring is configured to be rotatable to a position perpendicular to the long axis of the bed.

9. The inclined PET device according to claim 6, wherein the unit rings each are configured to be capable of parallel movement to a mutually coincident position.

10. The inclined PET device according to claim 8, wherein the unit rings each are configured to be capable of parallel movement in synchronization with a rotation of the unit rings.

11. The inclined PET device according to claim 1, further comprising detector units in which the plurality of the PET detectors are disposed in the direction of the long axis of the bed, the detector units being shifted little by little in the direction of the long axis of the bed so that the respective PET detectors are disposed and stacked in the direction parallel to the long axis of the bed.

12. The inclined PET device according to claim 11, wherein the detector units are configured to shift by variable amounts.

13. The inclined PET device according to claim 11, wherein main axes of the respective PET detectors are inclined according to amounts of shift of the detector units so that main axes are directed to a center point of the detector ring.

14. A PET combined device comprising:
the inclined PET device according to claim 1; and
a second device that performs a treatment or an examination in the open space of the inclined PET device.

15. The PET combined device according to claim 14, wherein the second device is a radiation therapy device.

16. The PET combined device according to claim 14, wherein the second device is a particle beam therapy device.

17. The PET combined device according to claim 14, wherein the second device is an X-ray transmission device.

18. The PET combined device according to claim 14, wherein the inclined PET device and the second device are integrally moved or rotated without interference with each other.

19. The PET combined device according to claim 14, wherein at least part of the second device is supported by the detector ring of the inclined PET device.

20. An inclined PET device comprising:
a detector ring; and
a plurality of PET detectors disposed in the detector ring, a cut plane of the detector ring being obliquely inclined so as not to intersect perpendicularly with a long axis of a bed that carries a subject to be examined,
wherein:
none of the PET detectors on opposite portions of the detector ring on either side of the bed overlap in at least one direction perpendicular to the long axis of the bed;
an open space with width for access is formed between the opposite portions of the detector ring in the at least one direction perpendicular to the long axis of the bed, the open space enabling access to the subject to be examined, the open space passing through the bed in the at least one direction perpendicular to the long axis thereof, and the open space being disposed in a direction that is the same as a direction of the access to the subject to be examined; and
the respective PET detectors are disposed and stacked in a direction parallel to the long axis of the bed.

21. An inclined PET device comprising:
a detector ring; and
a plurality of PET detectors disposed in the detector ring, edges of the detector ring being inclined at an angle oblique to a first axis perpendicular to a long axis of a bed for an examination subject, when viewed in a direction corresponding to a second axis perpendicular to the long axis of the bed;
wherein:
none of the PET detectors on opposite portions of the detector ring on either side of the bed overlap in a direction corresponding to the first axis perpendicular to the long axis of the bed, when viewed in the direction corresponding to the second axis perpendicular to the long axis of the bed;
an open space with width for access is formed between the opposite portions of the detector ring on either side of the bed, the open space being formed in the direction corresponding to the first axis perpendicular to the long axis of the bed, when viewed in the direction corresponding to the second axis perpendicular to the long axis of the bed, the open space enabling access to the examination subject, and the open space passing through the bed in the direction corresponding to the first axis perpendicular to the long axis of the bed, when viewed in the direction corresponding to the second axis perpendicular to the long axis of the bed; and
the respective PET detectors are disposed and stacked in a direction parallel to the long axis of the bed.

22. The inclined PET device according to claim 21, wherein the first axis is a horizontal axis and the second axis is a vertical axis.

* * * * *